United States Patent [19]

Revici

[11] Patent Number: 4,663,165

[45] Date of Patent: May 5, 1987

[54] METHOD FOR COUNTERACTING THE ADVERSE EFFECTS OF SODIUM CHLORIDE

[75] Inventor: Emanuel Revici, New York, N.Y.

[73] Assignee: Elena Avram, New York, N.Y.

[21] Appl. No.: 722,892

[22] Filed: Apr. 12, 1985

[51] Int. Cl.$^4$ .................... A61K 33/24; A61K 33/14; A61K 33/06

[52] U.S. Cl. .................... 424/131; 424/153; 424/154

[58] Field of Search .................... 424/131, 153, 154

[56] References Cited

U.S. PATENT DOCUMENTS

| | | | |
|---|---|---|---|
| 3,897,550 | 7/1975 | Reynolds | 424/154 |
| 3,993,751 | 11/1976 | Zinke | 424/128 |
| 4,202,887 | 5/1980 | Talbot | 424/154 |
| 4,213,784 | 7/1980 | Ikenoue et al. | 430/616 |
| 4,387,093 | 6/1983 | Lysaght | 424/131 |
| 4,499,078 | 2/1985 | Revici | 424/153 |

OTHER PUBLICATIONS

Chem. Abst. vol. 54:14592g, 1960.
Chem. Abst. vol. 46: 10448e 1952.

*Primary Examiner*—Johnnie R. Brown
*Assistant Examiner*—John W. Rollins
*Attorney, Agent, or Firm*—Pennie & Edmonds

[57] ABSTRACT

A composition comprising at least one compound containing a cation of magnesium, calcium, or strontium and an anion of bivalent negative sulfur or selenium, and at least one compound containing a cation of lithium or potassium and an anion of bivalent negative sulfur or selenium. Also, a composition comprising salt and the previously described compounds along with a method for counteracting the adverse effects of sodium chloride on a human body by administering to the body between about 0.5 and 10% of one of the disclosed compositions, preferably in a water solution.

22 Claims, No Drawings

METHOD FOR COUNTERACTING THE ADVERSE EFFECTS OF SODIUM CHLORIDE

TECHNICAL FIELD

This invention relates to new and useful improvements in a method for counteracting the deleterious effects of sodium chloride on the human body. More particularly, the invention relates to the administration of specific compositions or mixtures of compounds which are antagonists for sodium chloride.

BACKGROUND ART

It has become apparent in recent years that the ingestion of sodium chloride, especially at the higher levels to which humans have become accustomed, has deleterious effects, mainly related to the cardiovascular system, e.g., high blood pressure and arteriosclerosis. Such ingestion has also been shown to also encourage the growth of tumors. Efforts to restrict the ingestion of salt by eating low or unsalted food or substitute alternate condiments for salt has not been very successful. Therefore, it is preferred to develop non-toxic compounds which counteract the effects of salt and which can be ingested separately or along with the salt.

U.S. Pat. No. 4,499,078 suggests one method for achieving this result. The patent discloses that the anabolic effects of salt on a human body can be reduced by ingesting a compound which has an catabolic action. Specifically, the patent discloses that a magnesium compound containing bivalent negative sulfur may be taken with the salt or separately to offset the effects of the salt on the body. The content of that patent is expressly incorporated by reference herein.

The present invention relates to an improvement in such compounds for more effective counteraction of the deleterious effects of sodium chloride on the body, particularly with regard to the effect of sodium chloride on neoplastic diseases.

SUMMARY OF THE INVENTION

The invention relates to a composition comprising the combination of at least one compound containing a cation of magnesium, calcium, or strontium and an anion of bivalent negative sulfur or selenium, and at least one compound containing a cation of lithium or potassium and an anion of bivalent negative sulfur or selenium. A preferred bivalent negative sulfur is a thiosulfate or thiocyanate anion, and these compositions may also contain a compound containing a fluoride, silicon or oxygen anion. Advantageously, the magnesium, calcium or strontium compounds are present in an amount of about 2:1 to 20:1 of the lithium or potassium compounds.

The invention also relates to a composition comprising the combination of at least one of magnesium, calcium or strontium thiosulfate, at least one of magnesium, calcium, or strontium thiocyanate, and at least one of lithium or potassium thiosulfate. In this composition, the relative amounts of magnesium, calcium and strontium thiosulfate to magnesium calcium, and strontium thiocyanate to lithium or potassium thiosulfate ranges from about 2:1:1 to about 20:3:1. The composition can also include lithium or potassium fluoride.

An other embodiment of the invention includes compositions of sodium chloride along with the compounds described hereinabove. In these mixtures, the sodium chloride is present in an amount of about 66 to 90 weight percent and preferably between about 75 and 85 weight percent of the composition.

The invention also contemplates a method for counteracting the adverse effects of sodium chloride on the human body which comprises administering to the body one of the compositions described above. These compositions may or may not contain salt.

In this method, the amount of composition to be administered ranges from between 0.5 and 10% by weight, and preferably about 2%, in a water solution.

DETAILED DESCRIPTION OF THE PREFERRED EMBODIMENTS

In U.S. Pat. No. 4,499,078, it was established that the biological activity of various compounds with the body can be classified as either anabolic (constructive) or catabolic (destructive). It was also shown that sodium chloride has an anabolic effect, whereas compounds containing bivalent negative sulfur have a catabolic effect. Thus, the anabolic effect of the sulfur counteracts the anabolic effect of the sodium chloride. The manifest action of sodium chloride upon the appearance and growth of cancers has been established through several experiments. Tumors were produced by a transplant into the hind leg of rats and mice. These tumors were found to grow larger and more rapidly when the animals also received sodium chloride in their drinking water. The size and growth of the resultant tumors caused the animals to die earlier than those who did not ingest the salt.

In groups of 100 exbreeder mice of the strain $FC_1$, the number of spontaneous mammary tumors and the death from other conditions was recorded, during a one year observation. Spontaneous cancer was shown to be increased by the salt intake. In untreated animals, considered as controls, the average for 100 animals in one year observation was around 44% of spontaneous mammary cancers and of 15% death from other conditions than cancer. The addition of 2% salt in drinking water increased the spontaneous cancer to 65% for one year and a mortality of 20% from other conditions.

In animals injected intramuscularly with the carcinogens methylcholanthrene or benzyprene, the number of positive results was not only markedly increased but the tumors appeared earlier when the animals also ingested salt.

All these experiments are indicative of a marked enhancement upon the appearance, growth and malignant evolution of cancer by the action of ingested sodium chloride Statistical studies have also shown a relationship between the high intake of salt and arteriosclerosis. U.S. Pat. No. 4,499,078 showed that, in New Zealand rabbits, the intake of 2 g of cholesterol daily induced the appearance of aortic atheromatosis, and that the addition of salt in the drinking water increases the appearance of such atheromas.

The fact is that the diet of people in civilized countries includes an amount of salt which is about ten times higher than the amount considered to be necessary physiologically. Thus, applicant believes that the high occurrence of arteriosclerosis and even cancer may be at least partially attributed to this high sodium chloride intake.

A study of the biological action of the elements has shown the existence of antagonistic actions according to their reciprocal characters and position in the periodic table.

Besides the antagonism between the anabolic and catabolic elements which is related to the different series to which they belong, other antagonistic actions occur between elements in following positions in the same series. In the specific case of sodium, the first antagonism is seen for the catabolic elements, while the second for potassium and lithium, as immediately inferior and superior elements in the same A-1 series. Thus, in such a case a biological antagonistic action is found to correspond to the following cations: magnesium, calcium, strontium, potassium and lithium. Chlorine antagonists include the bivalent negative sulfur, bivalent negative selenium, silicon, fluorine and oxygen.

Especially active antagonists of the sodium chloride are the thiosulfates, thiocyanates, fluorides and chlorates of magnesium, calcium, strontium, potassium and lithium. To these, sodium or potassium chlorate may also be added due to their available oxygen.

Research has shown that each of these preparations has a salutary effect upon the noxious manifestations of the sodium chloride in cancer and arteriosclerosis.

While each one of these products has shown favorable effects by itself in the different experiments for counteracting the noxious effect of the administration of salt in cancer and arteriosclerosis, the concommitant use of two or more of these agents have shown improved results through what is believe to be synergistic action.

The antisodium agents are used as such or added to the salt preparations, and used together. Taste, smell and water solubility are the main criteria for choosing from the different compounds, those which are not changing the qualities of the salt when added to it.

It has been found that at least two of these agents in combination are very effective for counteracting the effects of salt. While any combination of bivalent negative sulfur containing compounds can be used, the most advantageous compounds to date are those containing a combination of nontoxic thiosulfates and thiocyanates. Preferably, at least one Group II thiosulfate or thiocyanate should be combined with at least one Group I thiosulfate or thiocyanate.

Specifically, the combination of magnesium or calcium thiosulfate or thiocyanate with either strontium, potassium or lithium thiosulfate or thiocyanate has been found to be suitable for preparing formulations of this additive. Also combinations of these components can be varied or mixed to provide additional formulations which would be suitable.

The following formulas were seen to give particularly good results:

| Component | Proportion (percent) | |
|---|---|---|
| | Agent A | Agent B |
| Magnesium thiosulfate | 6 | 10 |
| Magnesium thiocyanate | 3 | 3 |
| Calcium thiosulfate | 3 | 3 |
| Strontium thiosulfate | 1 | 1 |
| Potassium thiosulfate | 2 | 2 |
| Lithium fluoride | 0.03 | 0.05 |
| Sodium chloride | balance | balance |

In experiments using rats with Furth tumors transplanted in the hind leg, the administration of 2% salt in drinking water has increased the tumors (with an average, for 10 rats), to 30% more than in the untreated control rats. The use of a 2% mixture of the salt plus the antisodium chloride agents—has induced a manifest reduction of the tumor even with 10% below the controls without salt and of more than 35% for those having received sodium chloride alone. This action was markedly more manifest with the administration of the complex than with any compound alone, when added to the salt. From these experiments it has appeared advisable to use the modified salt to replace ordinary salt.

Mice and rats which received either of the specific complex salts listed above in drinking water for over 6 months did not exhibit any side effects. When these solutions were given to young animals, their growth was not observed to be different from that of the control group (i.e.—those which received no solution).

Based upon these experiments in animals, the continuous use of the corrected salt may have a basic influence upon both cancer and arteriosclerosis in humans as well.

While it is apparent that the invention herein disclosed is well calculated to fulfill the objects above stated, it will be appreciated that numerous modifications and embodiments may be devised by those skilled in the art, and it is intended that the appended claims over all such modifications and embodiments as fall within the true spirit and scope of the presnt invention.

What is claimed is:

1. A composition for counteracting the deleterious effects of sodium chloride comprising:
   at least one compound containing a cation of magnesium, calcium or strontium and an anion of thiosulfate, thiocyanate, fluoride, or chlorate; and
   at least one compound containing a cation of lithium or potassium and an anion of thiosulfate, thiocyanate, fluoride, or chlorate;
   wherein said magnesium, calcium, or strontium compounds are present in an amount of about 2:1 to 20:1 of said lithium or potassium compounds.

2. The composition of claim 1 further comprising sodium or potassium chlorate.

3. The composition of claim 1 further comprising sodium chloride; wherein the sodium chloride is present in an amount of about 66 to 90 weight percent of the total composition.

4. The composition of claim 3 wherein the sodium chloride content is about 75 to 85 weight percent of the total composition.

5. A composition for counteracting the deleterious effects of sodium chloride comprising:
   at least one of magnesium, calcium or strontium thiosulfate;
   at least one of magnesium, calcium, or strontium thiocyanate; and
   at least one of lithium or potassium thiosulfate;
   wherein the relative amounts of magnesium, calcium or strontium thiocyanate to lithium or potassium thiosulfate ranges from about 2:1:1 to 20:3:1.

6. The composition of claim 5 further comprising lithium or potassium fluoride.

7. The composition of claim 5 further comprising sodium chloride; wherein the sodium chloride is present in an amount of about 66 to 90 weight percent of the total composition.

8. The composition of claim 7 wherein the sodium chloride content is about 75 to 85 weight percent of the total composition.

9. A method for counteracting the adverse effect of sodium chloride on the human body which comprises administering to said body an effective amount of the composition of claim 1.

10. A method for counteracting the adverse effects of sodium chloride in the human body which comprises administering to said body an effective amount of the composition of claim 5.

11. A method for counteracting the adverse effects of sodium chloride on the human body which comprises administering to said body an effective amount of the composition of claim 6.

12. A method for counteracting the adverse effects of sodium chloride on the human body which comprises administering to said body an effective amount of the composition of claim 3.

13. The method of claim 12 wherein the amount of composition to be administered ranges from between 0.5 and 10% by weight of the composition in water.

14. A method for counteracting the adverse effects of sodium chloride on the human body which comprises administering to said body an effective amount of the composition of claim 7.

15. The method of claim 14 wherein the amount of composition to be administered ranges from between 0.5 and 10% by weight of the composition in water.

16. A method for counteracting the adverse effects of sodium chloride on the human body which comprises administering to said body an effective amount of the composition of claim 4.

17. The method of claim 16 wherein the amount of composition to be administered ranges from between 0.5 and 10% by weight of the composition in water.

18. The method of claim 17 wherein the amount of composition is about 2% by weight of the composition in water.

19. A method for counteracting the adverse effects of sodium chloride on the human body which comprises administering to said body an effective amount of the composition of claim 8.

20. The method of claim 19 wherein the amount of composition to be administered ranges from between 0.5 and 10% by weight of the composition in water.

21. The method of claim 20 wherein the amount of composition is about 2% by weight of the composition in water.

22. A method for counteracting the adverse effects of sodium chloride on the human body which comprises administering to said body an effective amount of the composition of claim 2.

* * * * *